(12) United States Patent
Won et al.

(10) Patent No.: US 11,574,552 B2
(45) Date of Patent: Feb. 7, 2023

(54) METHOD AND APPARATUS OF DIAGNOSTIC TEST

(71) Applicant: KNOWLEDGE AI INC., Boston, MA (US)

(72) Inventors: Joon Hee Won, Seoul (KR); Min Chol Kang, Seoul (KR)

(73) Assignee: Knowledge AI Inc., Boston, MA (US)

(*) Notice: Subject to any disclaimer, the term of this patent is extended or adjusted under 35 U.S.C. 154(b) by 405 days.

(21) Appl. No.: 16/405,284

(22) Filed: May 7, 2019

(65) Prior Publication Data
US 2019/0347953 A1 Nov. 14, 2019

(30) Foreign Application Priority Data

May 11, 2018 (KR) .................. 10-2018-0054280
Jan. 17, 2019 (KR) .................. 10-2019-0006407

(51) Int. Cl.
- G09B 7/02 (2006.01)
- G09B 7/07 (2006.01)
- G09B 19/00 (2006.01)
- G06F 3/0354 (2013.01)
- G06F 3/04883 (2022.01)

(52) U.S. Cl.
CPC ......... *G09B 19/00* (2013.01); *G06F 3/03545* (2013.01); *G06F 3/04883* (2013.01); *G09B 7/02* (2013.01); *G09B 7/07* (2013.01)

(58) Field of Classification Search
CPC ............. G09B 19/00; G09B 7/02; G09B 7/07
USPC ........................................................ 434/238
See application file for complete search history.

(56) References Cited

U.S. PATENT DOCUMENTS

| 6,215,901 B1 | 4/2001 | Schwartz |
| 11,073,921 B2 | 7/2021 | Weidler et al. |
| 2007/0105079 A1 | 5/2007 | O'Toole et al. |

(Continued)

FOREIGN PATENT DOCUMENTS

| CN | 106470608 | 3/2017 |
| JP | 2009031614 A | 2/2009 |

(Continued)

OTHER PUBLICATIONS

Won, Jun-Hui, Notice of Reason for Refusal against KR Patent Application No. 10-2019-0006407 (including English translation) dated Mar. 20, 2019, 13 pages.

(Continued)

*Primary Examiner* — Thomas J Hong
(74) *Attorney, Agent, or Firm* — Fish & Richardson P.C.

(57) ABSTRACT

Method, apparatus and computer program for providing a personalized study plan to a learner through cognitive and behavioral diagnosis of the learner. A learner who uses a data input device such as a smart pen and a stylus pen by using data obtained from the data input device. The method, apparatus and computer program relate to technology for obtaining input data based on information inputted by a user for at least one question with the data input device, creating test behavior data on the user from the obtained input data, analyzing cognition and behavior of the user based on at least one of metadata on the at least one question and the created test behavior data, and providing a personalized study plan to the user through an algorithm using machine learning based on the cognition and behavior analysis.

13 Claims, 12 Drawing Sheets

(56) References Cited

U.S. PATENT DOCUMENTS

| | | |
|---|---|---|
| 2009/0003705 A1 | 1/2009 | Zou et al. |
| 2010/0021022 A1 | 1/2010 | Pittel et al. |
| 2010/0104189 A1 | 4/2010 | Aravamudhan et al. |
| 2011/0188783 A1 | 8/2011 | Minoni et al. |
| 2013/0085955 A1 | 4/2013 | Dugas |
| 2013/0109003 A1* | 5/2013 | Lee .................. G09B 7/00 434/362 |
| 2013/0207937 A1 | 8/2013 | Lutian et al. |
| 2013/0229390 A1 | 9/2013 | DiVerdi et al. |
| 2013/0257777 A1 | 10/2013 | Benko et al. |
| 2014/0272840 A1 | 9/2014 | Peterson et al. |
| 2018/0350015 A1* | 12/2018 | Gordon .................. G06N 20/00 |
| 2020/0278760 A1 | 9/2020 | Kämpf |
| 2021/0132709 A1 | 5/2021 | Tatani et al. |

FOREIGN PATENT DOCUMENTS

| | | |
|---|---|---|
| JP | 2015161892 A | 9/2015 |
| KR | 10-2010-0132217 A | 12/2010 |
| KR | 101581921 B1 | 12/2015 |
| KR | 101811543 B1 | 12/2017 |
| WO | 2012127798 A1 | 9/2012 |

OTHER PUBLICATIONS

Won, Jun-Hui et al., Notice of Reason for Refusal against KR Patent Application No. 10-2018-0054280 (including English translation) dated Aug. 21, 2018, 9 pages.

Extended European Search Report dated Sep. 5, 2019 relating to European Patent Application No. 19166845.8, 11 pages.

* cited by examiner

- Page:0.329.3244.0.54
- Page:0.329.3244.0.55
- Page:0.329.3244.0.56
- Page:0.329.3244.0.57
- Page:0.329.3244.0.58
  - Stroke: 1
    - Coordinate. x: 051.94 y: 053.70 force: 070 time: 2017-10-26 11:13:52.624
    - Coordinate. x: 051.75 y: 053.74 force: 062 time: 2017-10-26 11:13:52.636
    - Coordinate. x: 051.79 y: 053.93 force: 058 time: 2017-10-26 11:13:52.649
    - Coordinate. x: 051.75 y: 054.19 force: 054 time: 2017-10-26 11:13:52.663
    - Coordinate. x: 051.79 y: 054.71 force: 049 time: 2017-10-26 11:13:52.676
    - Coordinate. x: 051.79 y: 055.35 force: 046 time: 2017-10-26 11:13:52.689
    - Coordinate. x: 051.75 y: 056.03 force: 045 time: 2017-10-26 11:13:52.700
    - Coordinate. x: 051.68 y: 056.59 force: 044 time: 2017-10-26 11:13:52.714
    - Coordinate. x: 051.64 y: 056.93 force: 044 time: 2017-10-26 11:13:52.728
    - Coordinate. x: 051.64 y: 057.04 force: 043 time: 2017-10-26 11:13:52.742
    - Coordinate. x: 051.71 y: 057.11 force: 043 time: 2017-10-26 11:13:52.753
    - Coordinate. x: 051.86 y: 057.11 force: 043 time: 2017-10-26 11:13:52.767
    - Coordinate. x: 052.24 y: 057.19 force: 043 time: 2017-10-26 11:13:52.781
    - Coordinate. x: 052.73 y: 057.08 force: 043 time: 2017-10-26 11:13:52.792
    - Coordinate. x: 053.36 y: 057.04 force: 043 time: 2017-10-26 11:13:52.806
    - Coordinate. x: 054.00 y: 056.93 force: 054 time: 2017-10-26 11:13:52.820
    - Coordinate. x: 054.56 y: 057.00 force: 066 time: 2017-10-26 11:13:52.835
    - Coordinate. x: 054.94 y: 057.00 force: 188 time: 2017-10-26 11:13:52.847
    - Coordinate. x: 055.16 y: 057.04 force: 255 time: 2017-10-26 11:13:52.860
  - Stroke: 2
  - Stroke: 3
  - Stroke: 4
  - Stroke: 5
  - Stroke: 6
  - Stroke: 7
  - Stroke: 8
  - Stroke: 9
  - Stroke: 10
  - Stroke: 11
  - Stroke: 12
  - Stroke: 13
  - Stroke: 14
  - Stroke: 15
  - Stroke: 16
  - Stroke: 17
  - Stroke: 18
  - Stroke: 19

FIG. 4

| No. | Unit | Question Point | Total Score | OX | Concept Score | Process Score | Correct Rate | Understanding | Diagnostic Info Data | | | Behavior Pattern | Teacher's Opinion |
|---|---|---|---|---|---|---|---|---|---|---|---|---|---|
| | | | | | | | | | Analysis information | You | Mean | | |
| Q1 | Number | 10.0 | 10.0 | 10.0 | | | 80% | 89.8% | Solving time | 44.0 | 44.4 | Smoothly solved without delay. | |
| | | | | | | | | | Delay time | 21.2 | 124.2 | | |
| | | | | | | | | | N of strokes | 88.0 | 89.3 | | |
| | | | | | | | | | N of Delays | 7.0 | 15.3 | | |

FIG. 7

METHOD AND APPARATUS OF DIAGNOSTIC TEST

CROSS REFERENCE TO RELATED APPLICATIONS

This application claims priority to Korean Patent Application No. KR 10-2018-0054280, filed May 11, 2018 and Korean Patent Application No. KR 10-2019-0006407, filed on Jan. 17, 2019. The entire contents of the above applications are incorporated herein by reference.

BACKGROUND

The present invention relates to a diagnostic test, in particular a diagnostic test method, apparatus and computer program providing a personalized study plan through cognitive and behavioral analysis of a learner who uses a data input device such as a smart pen and a stylus pen by using data obtained from the data input device.

Typically, a learner may solve questions of a diagnostic test and an instructor may grade the learner's answers to diagnose the learner through the learner's performance. With an increasing use of smart devices such as smartphones and tablet PCs these days, smart pens are increasingly used as means of input onto a touch screen of a smart device and an environment is being created in which a smart pen can be used for learning. This has enabled a learner to write on a particular type of a printed material with a smart pen, solve a question on the printed material, or mark an answer. A smart pen can create digital data from learner's notes based on recognition of a pattern including the dot pattern developed by Anoto.

Conventional tests of a learner focus only on whether the learner's answer is correct or not, without reviewing the process of the learner solving the question. Since diagnostic tests where a learner uses a smart pen also focus only on whether the learner's answer is correct or not, it can be said that the diagnostic tests still consist of evaluation of performances focused on results.

With the diagnostic tests, it is not possible to evaluate a learner by various standards. Accordingly, they can only obtain the learner's performance result and just provide exercise questions similar to the one that the learner presented an incorrect answer to. In addition, since diagnostic tests where a learner is diagnosed depending only on whether the learner's answer is correct or not even in an environment where the learner can learn using a smart pen do not sufficiently use a variety of data obtainable from a smart pen, which is a further advanced learning tool, an improved diagnostic test using it is in demand.

Meanwhile, with the rise of massively open online courses (MOOCs), use of data analysis for personalizing computer-based education is coming into wider use. However, the MOOCs are used only for a small portion of the student community. In particular, most students at the middle and high school levels still perform their tasks in an offline (classroom)-based educational environment that uses writing instruments and paper as the main tools to take tests. Since there has been no data collection mechanism operable in the environment, no benefits from personalization by data analysis could be had and evaluating test performances served as a considerable burden. Accordingly, provision of personalized education for a learner through analysis of data of a smart pen is in need.

SUMMARY

Aspects of the present invention has an object of diagnosing a user through the user's behavior pattern using a data input device.

The object of the present invention is to provide a system helping students achieve a better test result through a derivation of cognitive and behavioral factors that affect students' performances and a recommendation engine that can output personalized score improvement strategies. The system may be implemented through a data-driven and algorithmically calculated relationship between cognitive and behavioral factors associated with test-taking behavior and data specific about each student that are collected by a data input device such as a smart pen.

In an advancement from existing diagnostic tests focusing on result, aspects of the present invention is intended to perform a diagnostic test focused on process where it is determined whether a learner efficiently solves a question, solves a question quickly without hesitation, or has a difficulty "in regard to a particular concept or process" and where the student's behavior pattern is compared with those of excelling students to find difference between them.

Another aspect of the present invention is intended to perform analysis of cognition and behavior of a learner to determine "why" the learner exhibits a particular behavior pattern in regard to a particular concept or process. Provision of a personalized study plan to the learner through the cognition and behavior analysis is intended.

The present invention has been derived to achieve the objects above and suggests an invention capable of providing a personalized study plan to a user by a diagnostic test using a data input device.

An embodiment of the present invention sets forth a diagnostic test method using a data input device, comprising: obtaining input data based on information inputted by a user for at least one question with the data input device; creating test behavior data on the user from the obtained input data; and analyzing cognition and behavior of the user based on metadata on the at least one question and/or the created test behavior data.

A variety of input devices such as a smart pen and a stylus pen may be used as the data input device. The description below is focused on cases where a smart pen is used, but the present invention is not limited thereto. The diagnosis and analysis can be made in the same manner in cases where tests are taken using fingers in mobile devices (e.g., tablet PCs) or the like.

In a diagnostic test method using a data input device according to an embodiment of the present invention, the input data may comprise coordinate values of points forming a plurality of strokes and information on the time when the points are inputted, and the test behavior data may comprise a plurality of behavioral metrics.

In a diagnostic test method using a data input device according to an embodiment of the present invention, the analyzing cognition and behavior of the user may comprise: obtaining test behavior data for the at least one question from each of a plurality of users including the user; identifying at least one behavioral metric associated with each of at least one cognitive and behavioral diagnostic (CBD) factor; calculating z-score of the at least one behavioral metric of the user, the z-score being the value of the difference between the value (X) of the at least one behavioral metric of the user and the mean value ($\mu$) of the at least one behavioral metric associated with the CBD factor of the plurality of users divided by the standard deviation value ($\sigma$)

of the at least one behavioral metric associated with the CBD factor of the plurality of users; normalizing the z-score of the least one behavioral metric; calculating the weighted average of the normalized z-score based on a predetermined weight for the at least one behavioral metric; and determining a value of the CBD factor of the user from the calculated weighted average.

In a diagnostic test method using a data input device according to an embodiment of the present invention, the at least one CBD factor may comprise confidence, grit, reasoning, concept memory, deep understanding, calculation ability, ability to understand question, test-taking strategy, etc. and each of the CBD factors may be expressed with a function based on at least one different behavioral metric and/or metadata on the question.

Another embodiment of the present invention sets forth a diagnostic test method using a data input device comprising: obtaining the input data based on information inputted by a user for at least one question with the data input device; creating test behavior data on the user from the obtained input data; and providing a personalized study plan to the user based on metadata on the at least one question and/or the created test behavior data.

A diagnostic test method using a data input device according to another embodiment of the present invention may further comprise analyzing cognition and behavior of the user based on metadata on the at least one question and/or the created test behavior data.

In a diagnostic test method using a data input device according to another embodiment of the present invention, the providing a personalized study plan to the user may comprise: determining a value of at least one cognitive and behavioral diagnostic (CBD) factor for the at least one question for a plurality of users including the user; calculating, for each of the at least one CBD factor, a similarity among at least two questions comprising the at least one question and a similarity among the plurality of users; calculating, for each of the at least one CBD factor, a cognitive gap metric by using the similarity among the at least two questions and the similarity among the plurality of users; and recommending a question to the user based on the calculated cognitive gap metric.

In a diagnostic test method using a data input device according to another embodiment of the present invention, the calculating a similarity among at least two questions comprising the at least one question and a similarity among the plurality of users may comprise applying a cosine similarity function.

In a diagnostic test method using a smart pen according to another embodiment of the present invention, the recommending a question to the user may comprise: producing the calculated cognitive gap metric for each of combinations of the user and the at least one question; identifying a question having the highest cognitive gap metric based on the calculated cognitive gap metric; and recommending the identified question to the user.

An embodiment of the present invention sets forth a diagnostic test apparatus using a data input device comprising a memory and a processor, wherein the processor is configured to obtain the input data based on information inputted by a user for at least one question with the data input device, create test behavior data on the user from the obtained input data, and analyze cognition and behavior of the user based on metadata on the at least one question and/or the created test behavior data.

In a diagnostic test apparatus according to an embodiment of the present invention, the processor may be further configured to provide a personalized study plan to the user based on the cognition and behavior analysis.

In a diagnostic test apparatus according to an embodiment of the present invention, the processor may be further configured to obtain test behavior data for the at least one question from each of a plurality of users including the user, identify at least one behavioral metric associated with each of at least one cognitive and behavioral diagnostic (CBD) factor, calculate z-score of the at least one behavioral metric of the user, the z-score being the value of the difference between the value (X) of the at least one behavioral metric of the user and the mean value ($\mu$) of the at least one behavioral metric associated with the CBD factor of the plurality of users divided by the standard deviation value ($\sigma$) of the at least one behavioral metric associated with the CBD factor of the plurality of users, normalize the z-score of the least one behavioral metric, calculate the weighted average of the normalized z-score based on a predetermined weight for the at least one behavioral metric, and determine a value of the CBD factor of the user from the calculated weighted average.

In a diagnostic test apparatus according to an embodiment of the present invention, the processor may be further configured to determine a value of at least one cognitive and behavioral diagnostic (CBD) factor for the at least one question for a plurality of users including the user, calculate, for each of the at least one CBD factor, a similarity among at least two questions comprising the at least one question and a similarity among the plurality of users, calculate, for each of the at least one CBD factor, a cognitive gap metric by using the similarity among the at least two questions and the similarity among the plurality of users, and recommend a question to the user based on the calculated cognitive gap metric.

Another embodiment of the present invention sets forth a computer program stored in a medium to perform a diagnostic test method using a data input device, wherein the computer program comprises instructions to cause a computer or a processor to obtain input data inputted by a user for at least one question with the data input device, create test behavior data on the user from the obtained input data, analyze cognition and behavior of the user based on metadata on the at least one question and/or the created test behavior data, and provide a personalized study plan to the user based on the cognition and behavior analysis.

A computer program stored in a medium according to another embodiment of the present invention may comprise instructions to perform each step of the above-mentioned diagnostic test methods using a data input device.

In a diagnostic test method using a smart pen according to an embodiment of the present invention, the creating test behavior data may comprise calculating a total time of use of the smart pen by the user, and it may comprise calculating a time of preparation by the user before inputting information on the at least one question and calculating a total time of input of information by the user with the smart pen.

In a diagnostic test apparatus according to another embodiment of the present invention, wherein to create test behavior data, the processor may be further configured, for the purpose of calculating a total time of use of the smart pen by the user, to calculate a time of preparation by the user before inputting information using the smart pen and calculate a total time of input of information by the user with the smart pen.

By way of the present invention, it is possible to provide a cognitive and behavioral analysis result and a personalized study plan to a learner using a data input device through cognitive and behavioral analysis of the learner.

Additionally, the present invention is capable of providing a personalized study plan to a learner through machine learning algorithm using artificial intelligence.

BRIEF DESCRIPTION OF THE DRAWINGS

The attached drawings that are included herein and consist of part of this specification illustrate exemplary embodiments of the present invention and serve to describe characteristics of the invention, together with the above-mentioned general description and the detailed description provided below.

FIG. 4 is a diagram showing input data (raw data) obtained from a smart pen according to an example of the present invention.

FIG. 7 is an exemplary diagram showing a result of a diagnostic test according to an example of the present invention.

DETAILED DESCRIPTION

Various embodiments will be described in detail with reference to the attached drawings. Wherever possible, reference numbers will be used throughout the drawings to refer to the parts respectively corresponding to them or parts similar thereto. References made to specific examples and embodiments are for illustrative purposes only, and are not intended to limit the scope of the invention or the claims.

Whenever a constituent is referred to as "comprising" another constituent in the description of the invention or the claims, it is not to be construed as consisting of the constituent only, unless otherwise stated, and should be understood as a constituent that possibly further comprises other constituents.

Examples of the present invention are hereinafter described in further detail with reference to the drawings.

Figure 1:
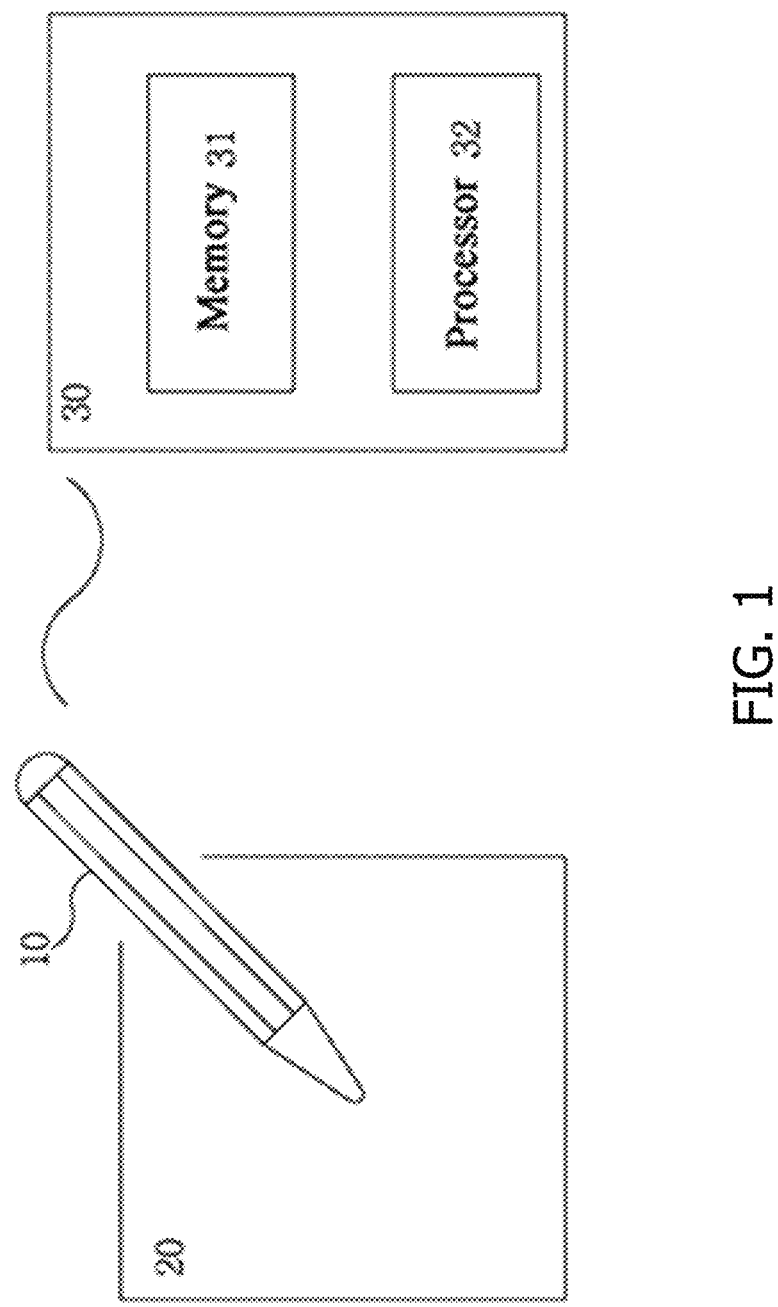
FIG. 1 shows a system for providing a diagnostic test using a smart pen according to various examples of the present invention.

FIG. 1 shows a system for conducting a diagnostic test relating to an example of the present invention. A learner can solve at least one question presented for the diagnostic test and derive an answer. In order to solve at least one question, the learner also may write on the printed material (20) such as a diagnostic test sheet by using the smart pen (10) as with a pencil or a pen. The learner using the smart pen (10) may hereinafter be referred to as "the user." In addition, "student," "learner" and "user" may be used in an interchangeable manner in the following descriptions.

The printed material (20) needs to be one capable of recognizing information inputted by the smart pen (10), for example, the one where a pattern such as a dot pattern is formed, rather than a piece of ordinary paper. To this end, a designated file can be manufactured by a designated printer.

A question for a diagnostic test presented on the printer material (20) is preferably not a question that can be solved by simple memorization. That is, the question is preferably the one where a strategy is required to solve it and the solving process needs to be stated in order to reach a conclusion. For example, a type of question with a narrow choice of strategy such as calculation may be useful for analyzing data for diagnosis of the learner. However, if a question is too easy for the level of the learner, the question may not be appropriate because the learner may derive the answer upon reading it without using the smart pen. In addition, an answer to a subjective question may be easier for data analysis than that of an objective question (multiple choice). Of the subjective questions, a short-answer question may be easier for data analysis than an essay question because an essay question has a broad range of answers depending on how students express them.

The smart pen (10) as a data collecting device may comprise a camera (not shown) for recognition of a pattern inputted in the printed material (20) and a short distance communication module for transmitting data to the diagnostic test apparatus (30). This may enable real-time transmission of data from the smart pen (10) by streaming. When a diagnostic test is conducted with the smart pen (10), it is necessary to check whether or not it is sufficiently charged (90% or more) before use and to check whether or not data are normally transmitted from the smart pen (10).

When the learner solves at least one question in the printed material (20) using the smart pen (10), the diagnostic test apparatus (30) for diagnosing the learner may carry out a method for diagnostic tests according to the various examples of the present invention that are described below in further detail.

Specifically, the diagnostic test apparatus (30) may comprise the memory (31) and the processor (32). By way of the processor (32), each step of the diagnostic test method according to the present invention can be performed and, in addition, a plurality of pieces of information such as data for diagnostic tests and diagnostic test result data, for example, may be stored in the memory (31) connected to the processor. The diagnostic test apparatus (30) may be, for example, a mobile device (e.g., a tablet PC) or a computer paired with the smart pen (10). It may also be connected to a server or used as a server. Not all constituents of the diagnostic test apparatus (30) are shown; it is well known to a skilled person in the art that it may comprise a communication module, a user interface, a display, etc.

Meanwhile, the diagnostic test methods described herein may be carried out by a computer or a processor using a computer program stored in a medium. That is, the computer program stored in a medium according to the present invention may comprise instructions that cause hardware, such as a computer or a processor, to perform the methods described herein.

Figure 2:
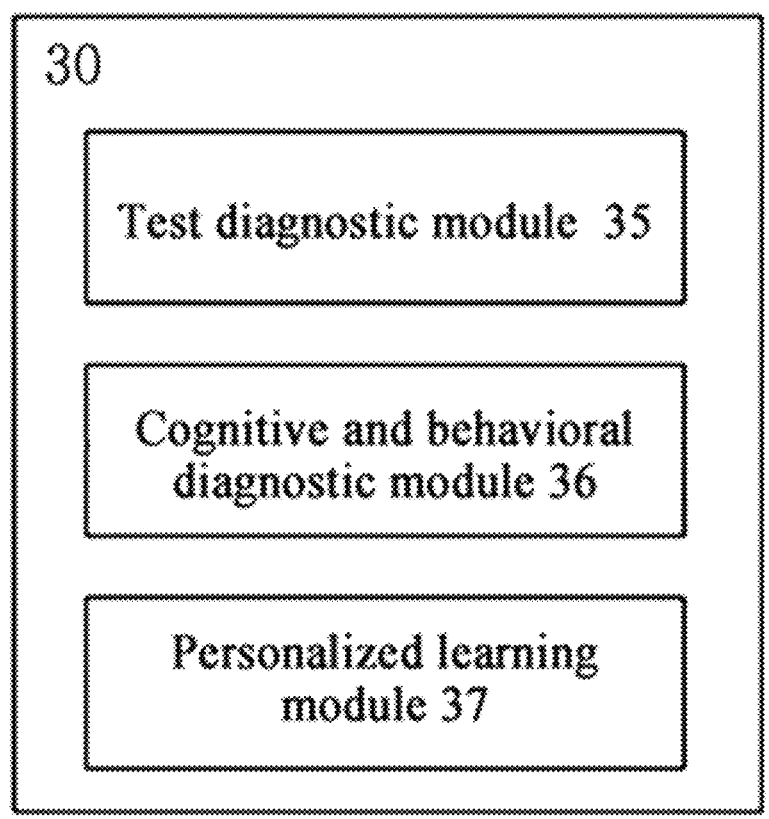
FIG. 2 is a block diagram showing the constitution of the diagnostic test apparatus of the present invention.

FIG. 2 is a block diagram showing a constitution of the diagnostic test apparatus (30) of the present invention. The diagnostic test apparatus (30) may comprise the test diagnostic module (35), the cognitive and behavioral diagnostic module (36), and the personalized learning module (37), which perform the diagnostic test methods described herein.

The test diagnostic module (35) may perform each step for conducting the diagnostic test method (300) using a smart pen. That is, the diagnostic test apparatus carrying out the diagnostic test method (300) described hereinafter may be the test diagnostic module (35).

Figure 3:
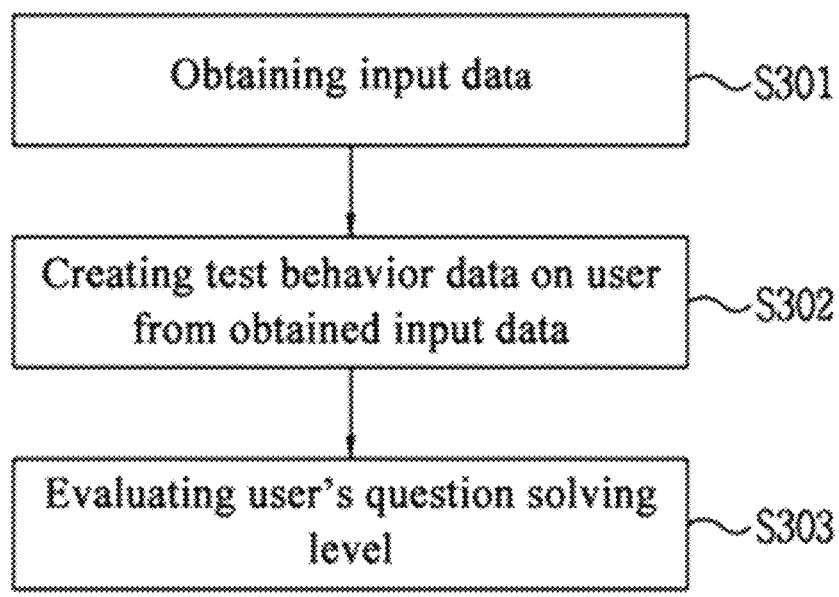
FIG. 3 is a flow chart of a diagnostic test method according to various examples of the present invention.

With reference to FIG. 3, the diagnostic test method (300) using a smart pen is described in further detail as below.

First, a user may enter information such as question solving with the smart pen on the printed material for at least one question presented for the diagnostic test. Then, the diagnostic test apparatus may perform a step (S301) of obtaining input data of the smart pen based on the information inputted by the smart pen.

The step of obtaining input data of the smart pen may comprise a step of identifying a page inputted by the user with the smart pen and a step of identifying at least one of a plurality of strokes inputted on the page, coordinate values of points forming each of the plurality of strokes, information on time when the points are inputted, and writing pressure of the points.

For example, FIG. 4 shows input data that may be obtained from the smart pen. A plurality of strokes (Stroke 1, Stroke 2, Stroke 3, and Stroke N) on a particular page may be identified. For example, a stroke may be specified by a continuous trajectory from a pen down point to a pen up point of the smart pen, and the coordinates from the pen down point to the pen up point may be recorded at specific time intervals (e.g., 0.012 to 0.015 in FIG. 4). Accordingly, input data including XY coordinate values of points forming a stroke, information on the time when the points are inputted, and writing pressure of the points can be identified for each stroke. In an example shown in FIG. 4, it is understood that, in Stroke 1 among the plurality of strokes of the particular page, the initial point has the (X, Y) coordinates of (051.94, 053.70) and the writing pressure of 070 and was inputted on Oct. 26, 2017 at 11:13:52:624. As shown above, the number of all strokes and detailed data on each stroke may be extracted for each page.

Next, the diagnostic test apparatus may perform a step (S302) of creating test behavior data on the user from the obtained input data, as analysis information on the smart pen user associated with the at least one question.

Thus, the analysis information on the user associated with the at least one question may be referred to as the test behavior data on the user. The test behavior data (analysis information) may be created for each question in association with the at least one question and may be created for a plurality of users that can be identified by name, age, gender, etc. The test behavior data may comprise a plurality of behavioral metrics. Examples of the plurality of behavioral metrics include delay time, stroke length, count of pauses in input of specific durations, input speed at specific stages of testing, length of input, and rework but are not limited thereto.

Figure 5:
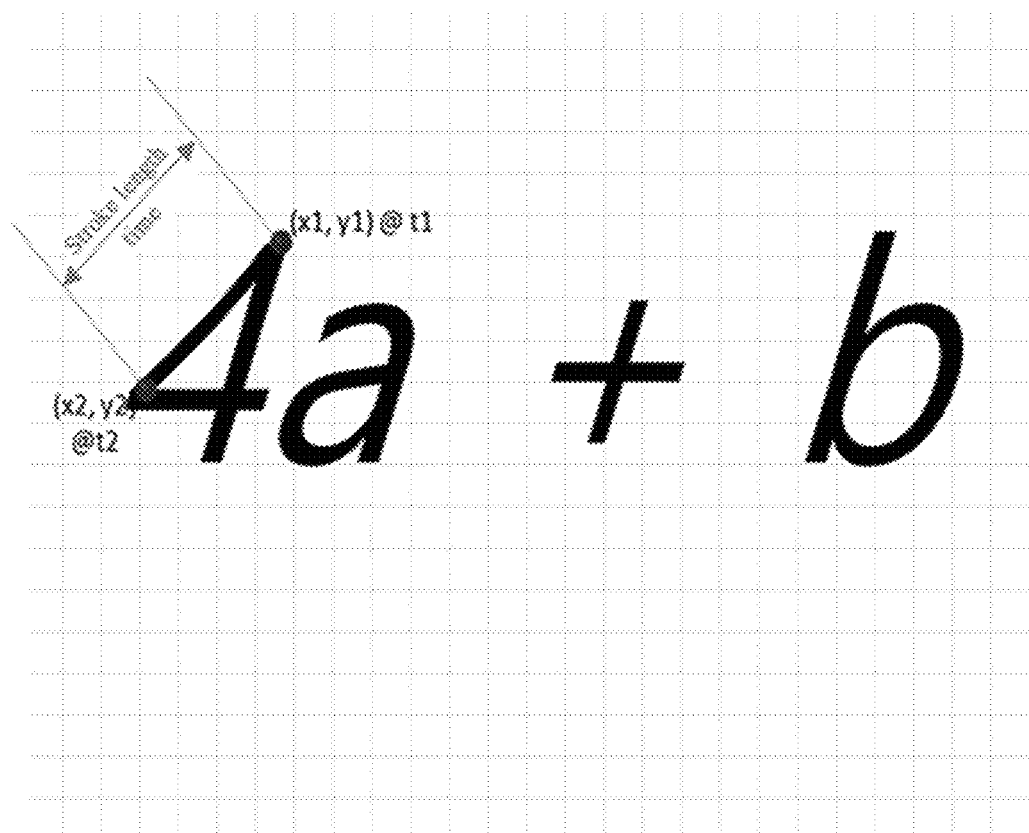
FIG. 5 is an example of a calculation for creating test behavior data from input data obtained from a smart pen according to an example of the present invention.

As exemplarily shown in FIG. 5, the diagnostic test apparatus considers stroke inputs as points in the two-dimensional Euclidean plane from the collected input data (e.g., stroke positions and time stamps) and applies a Cartesian geometric formula to calculate the distance and speed of input, thereby creating behavioral metrics. An example of behavioral metrics using the two stroke points (x1, y1) and (x2, y2) shown in FIG. 5 may be calculated as follows.

The distance between the two stroke points (x1, y1) and (x2, y2) may be calculated using the formula below:

$$\text{length} = \sqrt{(x_2-x_1)^2 + (y_2-y_1)^2}$$

The time between the two stroke points is given by:

$$\text{time duration} = t_2 - t_1$$

The input speed is given by:

$$\text{input speed} = \frac{\sqrt{(x_2-x_1)^2 + (y_2-y_1)^2}}{t_2 - t_1}$$

Alternatively, the test behavior data are described in further detail as below.

Delay time may be determined by the difference in the time stamps between the last stroke of one character and the first stroke of subsequent character. Count of pauses in input of specific durations may be determined by counting the number of time intervals during which no stroke is inputted. Length of input may be determined by the sum of the lengths of the strokes of all characters inputted by the user. Rework may be determined by a movement in the negative x-axis and/or the y-axis.

For the purpose of creating test behavior data for the user, the diagnostic test apparatus may calculate the number of all strokes (Total stroke) extractable from input data and calculate a total time of use of the smart pen by the user (Total time). A total time of use of the smart pen by the user for at least one question (Total time) may include a time when the user reads and deliberates on the at least one question after it is presented (Intro time) and a time when the question is actually solved with the smart pen (Solving time). Accordingly, the diagnostic test apparatus may calculate the time when the user reads and deliberates on the question (Intro time) and the time when the question is actually solved (Solving time). To this end, the time from a pen up point of the last stroke of the previous question to a pen down point of the first stroke of the next question, for example, may be defined as the deliberation time (Intro time).

More specifically, in order to create test behavior data on the user, the diagnostic test apparatus may track coordinates of points forming each stroke and, if the coordinate values of the points stay substantially the same for a predetermined time, determine that a delay has occurred. In addition, the diagnostic test apparatus may calculate a total time of delays and the number of delays (Number of Delays) occurred in association with the at least one question for the user. The predetermined time may be, for example, one second, two seconds, three seconds, four seconds, five seconds, etc. Different weights may be applied depending on the length of the predetermined time. Accordingly, a total time and the number of delays when the predetermined time is, for example, one second, two seconds, three seconds, four seconds or five seconds may be calculated.

In addition, the diagnostic test apparatus may additionally determine, as analysis information on the user associated with the at least one question, stroke-drawing speed (Stroke velocity, cm/second), initial speed of stroke (Initiation speed), ending speed (Ending speed), average speed (Average speed), solving speed, which is the number of strokes per question divided by a solving time per question (Solving velocity, strokes/time), sum of total length of strokes (Ink length), area used for solving (Area), complexity in directions of solving progression (Entropy), cross-out (Cross out), number of problems attempted (Problem attempted), number of changes in question solving order (Out of order), time taken to start solving the next question when the order of question solving has changed (Out of order time), etc.

For example, area used for solving (Area) may be calculated to be the area where strokes are present. Complexity in directions of solving progression (Entropy) may be calculated by determining that a stroke going from left to right or from top to bottom is of low entropy and, in contrast, a stroke going from right to left or from bottom to top is of high entropy. Cross-out may be traced by dividing it into cross-out of a number or a word (typo cross out), cross-out of part of problem solving process (problem solving cross out), and cross-out of the entire solving or an area corresponding thereto (big cross-out). Problem attempted may be calculated to be the number of times when a question is attended over a particular time. The number of changes in question solving order (Out of order) may be determined by tracking when the user skips a question to solve another question.

When the diagnostic test apparatus creates test behavior data including a plurality of behavioral metrics, the diagnostic test apparatus may perform a step (S303) of evaluating the user's question solving level for the question based on the created test behavior data.

Since the user's question solving level may be evaluated by a behavior pattern of the user determined by the user's behavior data, the step above may be referred to as a step of determining a behavior pattern of the user based on the created test behavior data. For example, if it is determined that the user has a behavior pattern of "smoothly solved without delay," the user's question solving level may be evaluated to be "smoothly solved without delay."

The diagnostic test apparatus may create test behavior data on a plurality of users associated with at least one question and store them in a memory. Alternatively, the diagnostic test apparatus may create analysis information such as test behavior data on a plurality of users associated with the at least one question and transmit it to a separate server or receive it from the server. The transmission and reception can be carried out in real time, according to which pieces of analysis information such as stored test behavior data may be updated periodically. The diagnostic test apparatus may compare pre-stored test behavior data with test behavior data created for the user in association with the at least one question. Instructors desiring to conduct a diagnostic test may share the at least one question on a network to accumulate data on a plurality of users, i.e., students, associated with the questions of the diagnostic test.

Additionally, when comparing pre-stored test behavior data with test behavior data created for the user in association with the at least one question, the diagnostic test apparatus may process the created test behavior data based on correlation among the at least one question. For example, when the user has test behavior data that noticeably differ from the pre-stored test behavior data for specific questions with high degree of correlation, more attention may be paid to the question solving level of that type of the specific questions.

Figure 6:
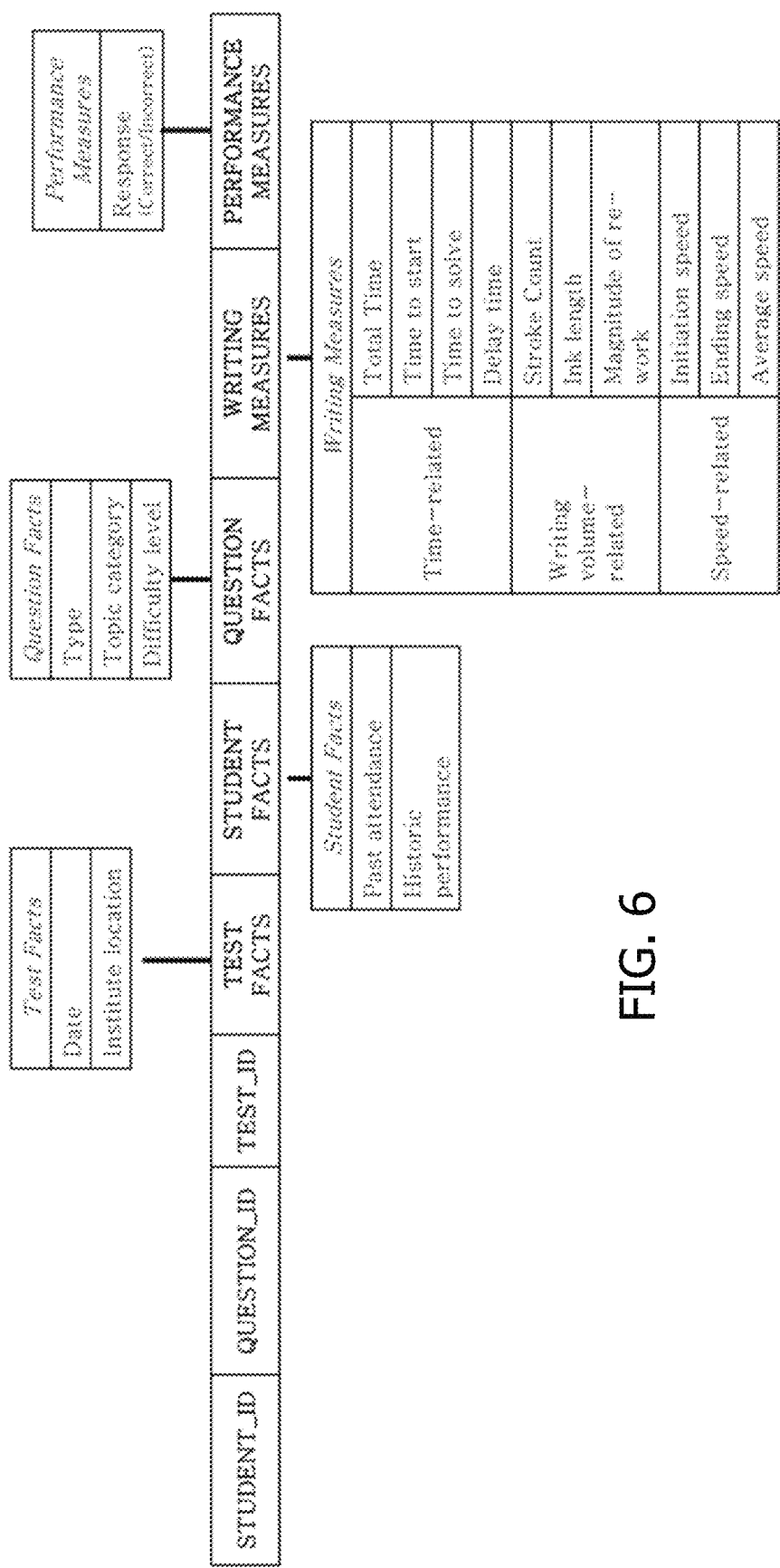
FIG. 6 shows an entire data structure according to an example of the present invention.

Further, the diagnostic test apparatus may use metadata on test questions for identification of the areas where the user shows strength or weakness. Metadata on a question may include information such as difficulty of the question, subject area of the question, and a proper student level for the question. Specifically, the test diagnostic module (35) may evaluate the user's question solving level by combining the test behavior data on the user and the metadata on the question, thereby determining the user's strengths and weaknesses. An example of the entire data structure that may be used in the test diagnostic module (35) and in the cognitive and behavioral diagnostic module (36) and the personalized learning module (37) described below is illustrated in FIG. 6. According to FIG. 6, the data structure used in the present invention may include not only wring measures (WRITING MEASURES) as the user's test behavior data and question facts (QUESTION FACTS) as metadata on the question but also identification information such as basic student identification information (STUDENT_ID), question identification information (QUESTION_ID), and test identification information (TEST_ID). It also may include data about test fact information (TEST FACTS) such as test date and place, student fact information (STUDENT FACTS) such as the student's past attendance and performances, and performance measures (PERFORMANCE MEASURES) representing the percentage of the student's correct responses.

Meanwhile, FIG. 7, which represents a diagnostic test result evaluating the user's question solving level based on the user's test behavior data for a particular question, shows, for example, a specific area of a report card. 'No.' indicates a question number; 'Unit' indicates a subject area (name of section); 'Question Point' indicates points assigned to the question; 'Total Score' indicates a total score, which is the sum of 'OX,' 'Concept Score' and "Process Score"; 'OX' indicates a score for presenting correct answers; 'Concept Score' indicates a score for application of concepts based on correct understanding thereof; 'Process Score' indicates a score for the process of solving the question, i.e., a score for how efficiently the question is solved using a strategy; and 'Correct Rate' indicates the percentage of correct answers. 'Understanding' becomes higher when a behavior pattern of the user associated with the question evaluated by the test behavior data is more similar to the patterns of the users who derived the correct answer. For example, a user who presented the correct answer but deliberated on the question for a long time or presented an incorrect answer following an erroneous question solving process and then corrected the answer after checking has a low score for 'Understanding.'

As shown in the diagnostic test result ("Diagnostic info Data") of FIG. 7, the diagnostic test apparatus may for example compare, as analysis information (test behavior data) on a plurality of users associated with the first question, the average values of the total number of stokes (Total stroke/N of strokes), the time taken to solve the question (Solving time), the total delay time (Delay time), and the number of delays (Number of Delays/N of Delays) of the plurality of users with the total number of strokes created (Total stroke), the time taken to solve the question (Solving time), the total delay time (Delay time), and the number of delays (Number of Delays/N of Delays) of a particular user associated with the first question, respectively.

For example, the average values of the time taken to solve the question, the delay time, the total number of strokes, and the number of delays of a plurality of users associated with the first question (Q1) are respectively 44.4, 124.2, 89.3 and 15.3 while the time taken to solve the question, the delay time, the total number of strokes, and the number of delays of the user associated with the first question (Q1) are 44.0, 21.2, 88.0, 7.0 respectively. Given this, the fact that the values are significantly lower than the average values of the plurality of users in the delay time and the number of delays may be considered in evaluation of the user's question solving level.

Figure 8:
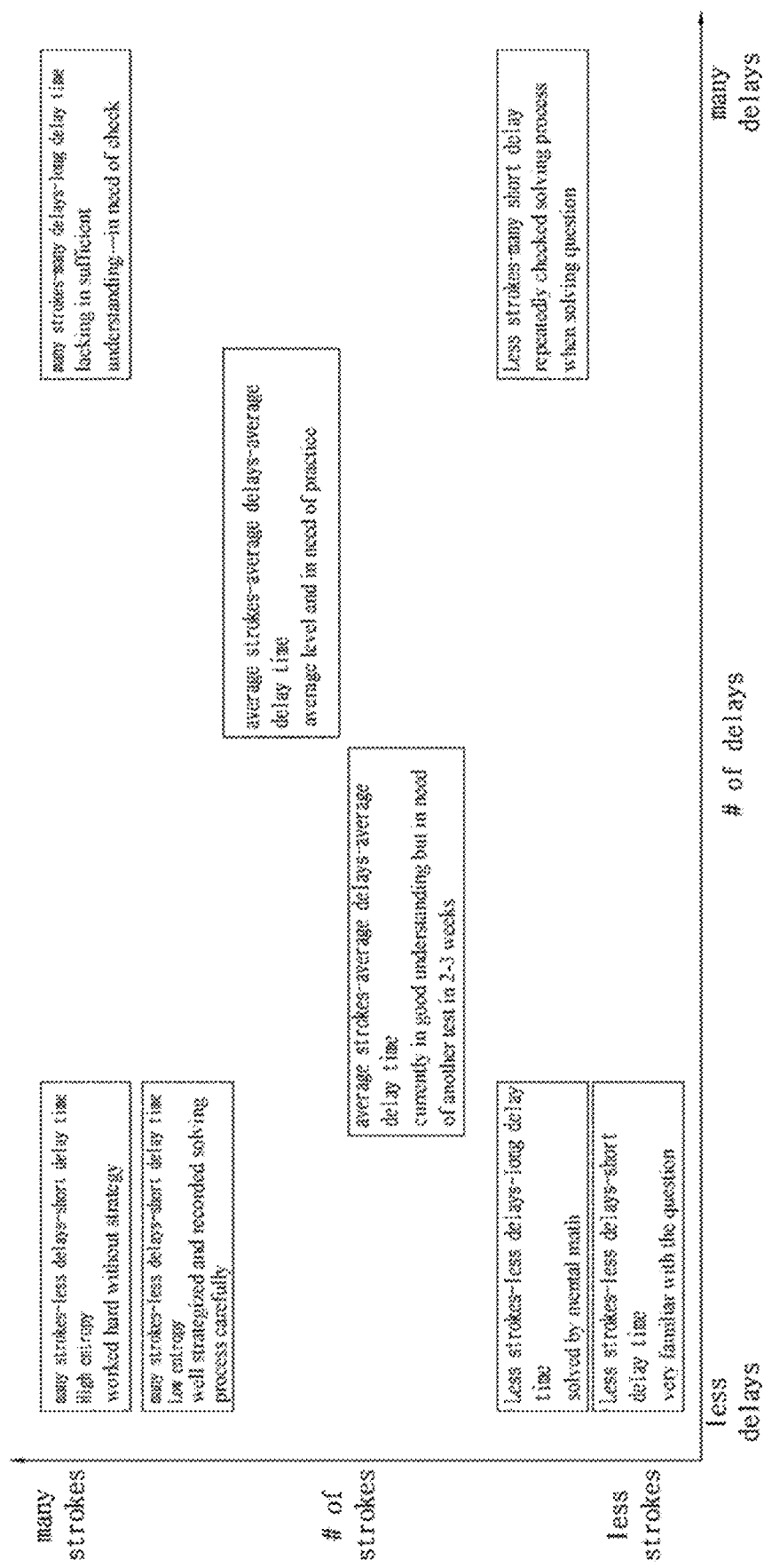
FIG. 8 is an exemplary diagram showing a result of a diagnostic test according to an example of the present invention.

That is, the diagnostic test apparatus may evaluate a question solving level of the particular user based on the comparison result above. In this regard, FIG. 8 shows, as an example, question solving levels of one or more users based on test behavior data including the total number of strokes and the number of delays.

First, in case of a user who is found to have a large number of strokes, a small number of delays, and a short delay time compared with predetermined criteria, the diagnostic test apparatus may additionally consider entropy. Accordingly, it may be evaluate a question solving level of a user having a high entropy to be "worked hard without strategy" and a question solving level of a user having a low entropy to be "well strategized and recorded solving process carefully."

Second, in case of a user who is found to have an average number of strokes, an average number of delays, an average delay time, the diagnostic test apparatus may consider detailed values of the pieces of information and evaluate the user to be "currently in good understanding but in need of another test in 2-3 weeks" or "average level and in need of practice."

Third, the diagnostic test apparatus may evaluate a question solving level of a user found to have a high number of strokes, a high number of delays, and a long delay time to be "lacking in sufficient understanding."

Fourth, for a user found to have a small number of strokes, a small number of delays, and a long delay time, the diagnostic test apparatus may evaluate "solved by mental math" and, for a user found to have a small number of strokes, a small number of delays, and a short delay time, the diagnostic test apparatus may evaluate "very familiar with the question."

Lastly, for a user having a small number of strokes and multiple, very short delays, it may evaluate "repeatedly checked solving process when solving question."

A diagnosis result of a question solving level of a user evaluated as illustrated in FIG. 8 may be displayed as a diagnosis result in the "Behavior Pattern" item shown in FIG. 7. This allows going beyond evaluation of the user simply depending on whether his/her answer to a question is correct or not so as to conduct analysis of behavior the user shows in the question solving process and find causes of the behavior, which enables a more efficient and effective teaching. For example, if a very long delay occurs in a user's question solving process that is longer than a particular time, relevant strokes may be displayed in a different color or a delay time may be tagged to the area of the strokes to more visually express a diagnosis result of the user's behavior. With this, an instructor may conceive a more effective teaching method to a learner.

As mentioned above, the diagnostic test apparatus may also use metadata on a question. FIGS. 7 and 8 only show a user's question solving level based on the user's test behavior data for a particular question. However, when it is combined with metadata on the question, it is possible to identify the types of questions for which the user has strengths or weaknesses. The test diagnostic module (35) may select a specific type of question (e.g., a question about geometry) particularly aimed to identify the user's strengths or weaknesses based on metadata on the question.

Meanwhile, the above-mentioned processes regarding FIGS. 3 to 8 may be carried out by the test diagnostic module (35) and descriptions about the test diagnostic module (35) may be applied to the processes.

The cognitive and behavioral diagnostic module (36) and the personalized learning module (37) included in the diagnostic test apparatus (30) of FIG. 2 are described below in further detail.

The cognitive and behavioral diagnostic module (36) and the personalized learning module (37) may perform each step for carrying out the diagnostic test method (900) using a smart pen. That is, the diagnostic test apparatus carrying out the diagnostic test method (900) described below may be the cognitive and behavioral diagnostic module (36) and/or the personalized learning module (37). Alternatively, the cognitive and behavioral diagnostic module (36) and/or the personalized learning module (37) may substantially perform some or all of the steps that the test diagnostic module (35) performs and may use output of the test diagnostic module (35).

Figure 9:
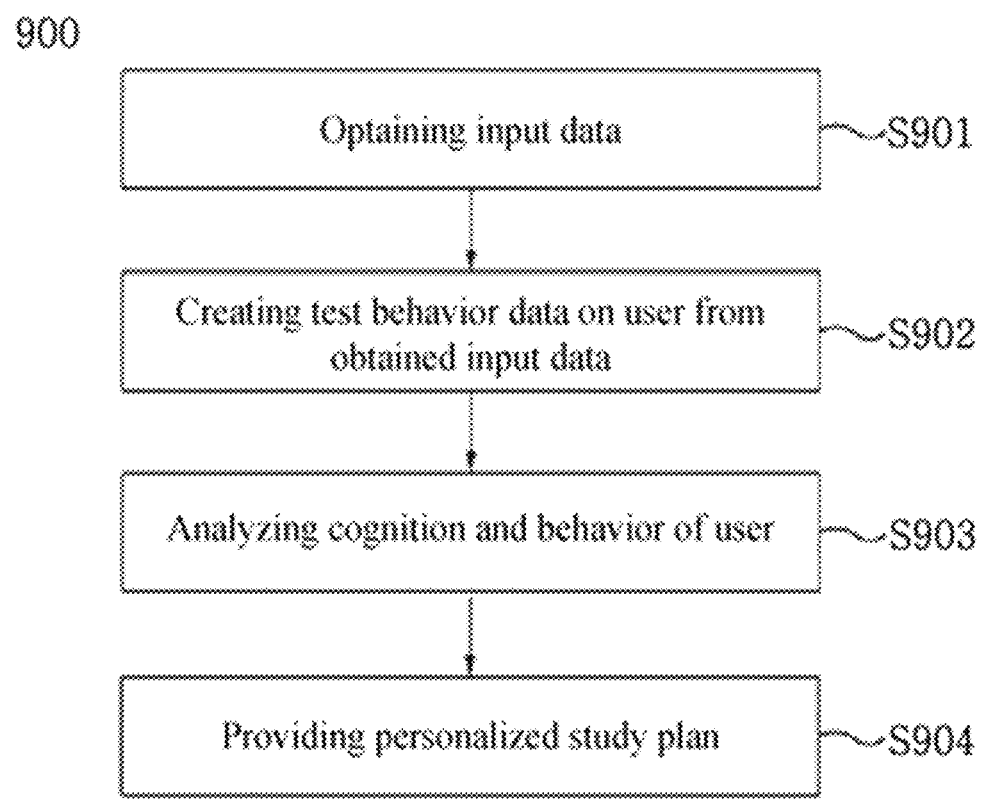
FIG. 9 is a flow chart of a diagnostic test method according to another example of the present invention.

The diagnostic test method (900) using a smart pen is described as below in further detail with reference to FIG. 9.

First, for at least one question presented for a diagnostic test, a user may input information such as question solving on a printed material with a smart pen. Then, the diagnostic test apparatus may perform a step (S901) of obtaining input data of the smart pen based on the information inputted by the smart pen.

Next, the diagnostic test apparatus may perform a step (S902) of creating test behavior data on the user from the obtained input data, as analysis information on the smart pen user associated with the at least one question. The detailed description relating to steps S301 and S302 illustrated in FIG. 3 may also be applied to steps S901 and S902 of FIG. 9. In addition, steps S901 and S902 may be performed by the test diagnostic module (35) and/or the cognitive and behavioral diagnostic module (36), and the cognitive and behavioral diagnostic module (36) may also receive output data of steps S901 and S902 performed by the test diagnostic module (35).

Next, the diagnostic test apparatus may perform a step (S903) of analyzing cognition and behavior of the user based on the test behavior data on the user and metadata on the question.

For example, with the cognitive and behavioral diagnostic module (36) such as a cognitive analysis engine, cognitive components such as confidence, grit, reasoning, concept memory, deep understanding, calculation ability, ability to understand question, test-taking strategy, focus, creativity, mental math speed, speed of understanding, carefulness, and flexibility may be derived. For example, the components may be defined as below. Grit may be an indicator showing the degree of grit with which a question is solved. Reasoning may be an indicator showing whether a test is taken with a logical reasoning. Concept memory may be an indicator showing whether concepts and formulae are accurately memorized and used. Calculation ability may be an indicator measuring calculation ability, which is one of basic mathematical abilities. Ability to understand question may be an indicator showing whether information in the question is accurately read and interpreted to build the right strategy. Test-taking strategy may be an indicator to identify whether question solving is strategically performed when taking a test. Focus may be an indicator showing an ability to maintain focus through questions that need substantial thinking. Creativity may be an indicator showing an ability to answer with short/creative responses relative to other students. Speed of understanding may be an indicator showing an ability to quickly and correctly understand questions and start answering. Carefulness may be an indicator of being risk-averse and double-checking answers. Flexibility may be an indicator showing an ability to successfully course-correct while answering a question.

The cognitive and behavioral diagnostic module (36) may apply data algorithms to a combination of the user test behavior data and metadata on a question attempted to show a score card of key underlying cognitive components having a significant impact on the user's performances. By showing underlying causes affecting the user's performances, the user is able to implement a more sustainable fix to his/her test behavior.

The cognitive and behavioral diagnostic module (36) may judge "cognitive components" such as confidence, reasoning, and concept memory associated with the user's cognition based on the user's test behavior data and metadata for a question. The cognitive and behavioral diagnostic module (36) may also analyze the user's "behavioral components" for question solving based on the user's test behavior data and metadata for a question. For example, it can perform judgment on the time when the user reads a question, judgment on the behavior of interpreting the question or the like based on test behavior data and metadata. That is, the cognitive and behavioral diagnostic module (36) may access "cognitive and behavioral components" of each student through numerical analysis of behavioral metrics calculated from data obtained by using a data collecting device such as a smart pen, and a cognitive and behavioral component may be referred to as a cognitive and behavioral diagnostics factor (CBD factor). Examples of CBD factors and behavioral metrics dependent to them are shown in Table 1.

Examples of metrics dependent to the CBD factor shown below may be considered.

Confidence stroke_gap time (total sum of time gaps between strokes when writing is not in progress): If this value is high, it may be considered that much deliberation was made when solving the question.

Count_of_long_pauses (total number of long deliberations): This value is high when the number of long deliberations is small and the value is low when the number of the deliberations is small.

Writing_speed (writing speed when solving the question): This considers not only comparison of speed among students but difference in speed of solving each question as the test progresses. Relatively confident and quick question solving results in a high value and a solving that is not results in a low value.

Initiation_speed (writing speed when the question solving begins): This indicates the speed of understanding the question and initiation of the question solving. For most students, the initiation speed of solving a question that they are familiar with and confident about is fast.

Grit

Stroke_length (total length of writing in the question solving): A high value means a relatively large amount of question solving.

Stroke_time (sum of the total time of writing): A longer solving time means a higher value.

Writing_speed (writing speed of question solving): Relatively confident and quick solving results in a high value and a solving that is not results in a low value.

Initiation_speed (writing speed when question solving begins): For most students, the initiation speed of solving a question that they are familiar with and confident about is fast.

Test Strategy

Figure 10:
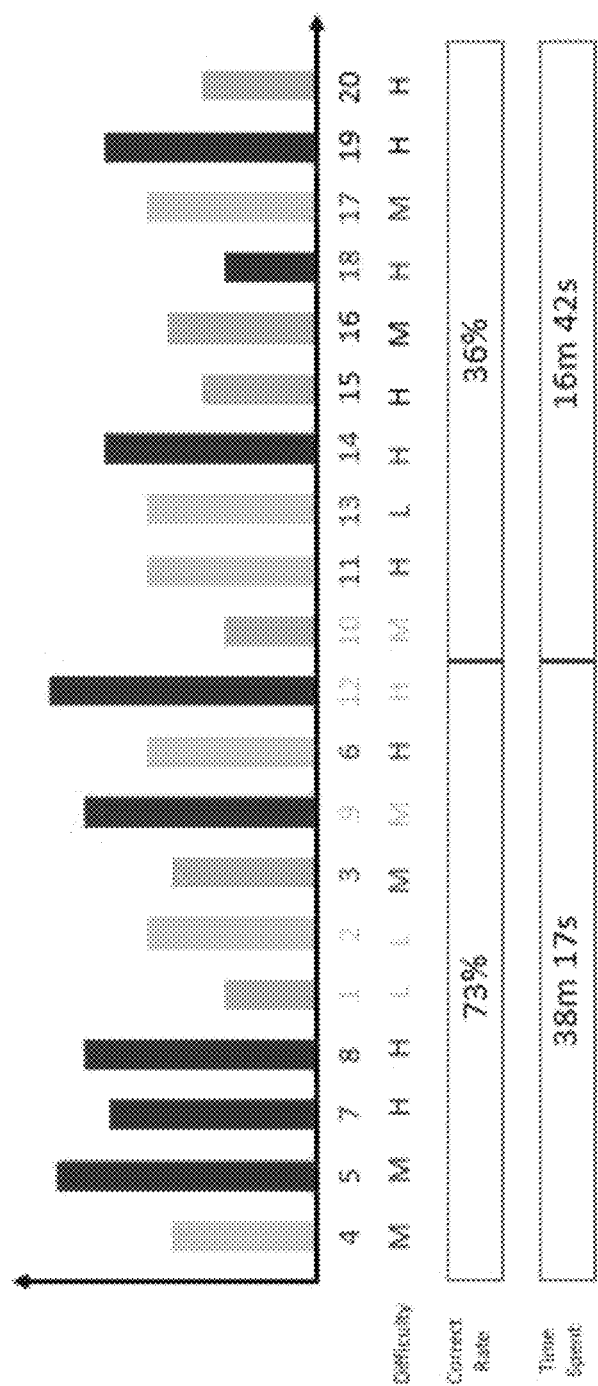
FIG. 10 is an exemplary graph illustrating a method for cognitive and behavioral diagnosis according to another example of the present invention.

FIG. 10 lists the question numbers in the order of solving the questions on the x-axis, and shows the time taken to solve each question on the y-axis. By, for example, calculating the percentage of correct answers and the amount of time taken for the first half and second half of the questions, an indicator to confirm whether the student strategically solves the questions that he/she can solve before other may be calculated.

Detailed contents on how to derive the CBD factor from the dependent metrics are shown below.

Step 1:

For a set of responses for each unique question, the cognitive and behavioral diagnostic module (36) may, at the student level, determine z-score of associated behavioral metrics. This is to determine a student's relative performance for a particular metric. Z-score may be given by the following formula:

$$z = \frac{X - \mu}{\sigma}$$

wherein X is the student's behavioral metric value for the question, μ is the mean value of the behavioral metrics across all responses to the question, and σ is the standard deviation of the behavioral metrics across all responses to the question.

Step 2:

The cognitive and behavioral diagnostic module (36) may normalize the z-score to a particular scale. For example, the cognitive and behavioral diagnostic module (36) may normalize the z-score to the scale of 1-10. This is to facilitate comparison of z-scores for different metrics. A normalized z-score may be given by the following formula:

TABLE 1

| CBD Factor | Type | Behavioral Metrics - Dependencies |
|---|---|---|
| Confidence | Cognitive | f(stroke_gap_time, count_of_long_pauses, writing_speed, initiation_speed, performance) |
| Grit | Behavioral | f(stroke_length, stroke_time, writing_speed, initiation_speed, performance) |
| Reasoning | Cognitive | f(reasoning_question_tag, total_time, performance) |
| Concept memory | Cognitive | f(concept_memory_tag, initial_time, performance) |
| Deep understanding | Cognitive | f(concept_application_tag, stroke_length, total_time, performance) |
| Calculation Ability | Behavioral | f(total_time, average_speed, performance) |
| Ability to understand question | Behavioral | f(concept_application_tag, initial_time, re-work, performance) |
| Test-taking Strategy | Behavioral | f(correct_rate_dip_second_half_vs_second_half, total_time_dip_second_half_vs_first_half) |

$$\text{Normalized } z\text{-score} = 1 + (z - \min(z)) \cdot \frac{10 - 1}{\max(z) - \min(z)}$$

wherein min(z) is the minimum value of the z-score for the behavioral metric among the set of responses, and max(z) is the maximum value of the z-score for the behavioral metric among the set of responses.

Step 3:

The cognitive and behavioral diagnostic module (36) may calculate the final score of a student for a particular CBD factor from a weighted average of the z-scores for various components of the CBD factor. With this, using the module, the system of the present invention may provide an in-depth understanding of cognitive factors that govern performances of the user. Accordingly, the cognitive and behavioral diagnostic module (36) may aim to cure a root cause of performance gaps, not simply resolving a superficial symptom.

The steps above are described as below with reference to FIG. 11.

The cognitive and behavioral diagnostic module (36) may perform a step (S1001) of filtering unique questions having a particular tag based on metadata on the questions. For example, when a plurality of users answer, using a smart pen, the unique questions having a particular tag, the obtained answers may be classified into correct answers and incorrect answers. For example, test behavior data may be obtained from each of the plurality of users. The step of filtering unique questions having a particular tag based on metadata on the questions may be skipped.

The cognitive and behavioral diagnostic module (36) may perform a step (S1002) of calculating z-score for each of at least one metric included in a predetermined functional formula associated with a CBD factor in order to derive the CBD factor. For example, z-score of a particular behavioral metric of a particular user may be calculated to be the value of the difference between the value (X) of the particular behavioral metric of the particular user and the mean value ($\mu$) of the particular behavioral metrics of a plurality of users divided by the standard deviation value ($\sigma$) of the particular behavioral metrics of the plurality of users.

The cognitive and behavioral diagnostic module (36) may perform a step (S1003) of normalizing the z-score calculated for each of at least one metric. For example, the cognitive and behavioral diagnostic module (36) may normalize the z-score to the scale of 1-10 or to the scale of 10-1. For example, z-score calculated for each of at least one metric included in a predetermined functional formula associated with a CBD factor may be normalized.

The cognitive and behavioral diagnostic module (36) may give a weighted average to normalized z-scores for at least one metric to determine the weighted average of the normalized z-scores as the value of the CBD factor (S1004). In addition, although not illustrated in FIG. 11, the weighted average of the scores may be further weighted (e.g., age-weighted) based on other factors.

Figure 11:
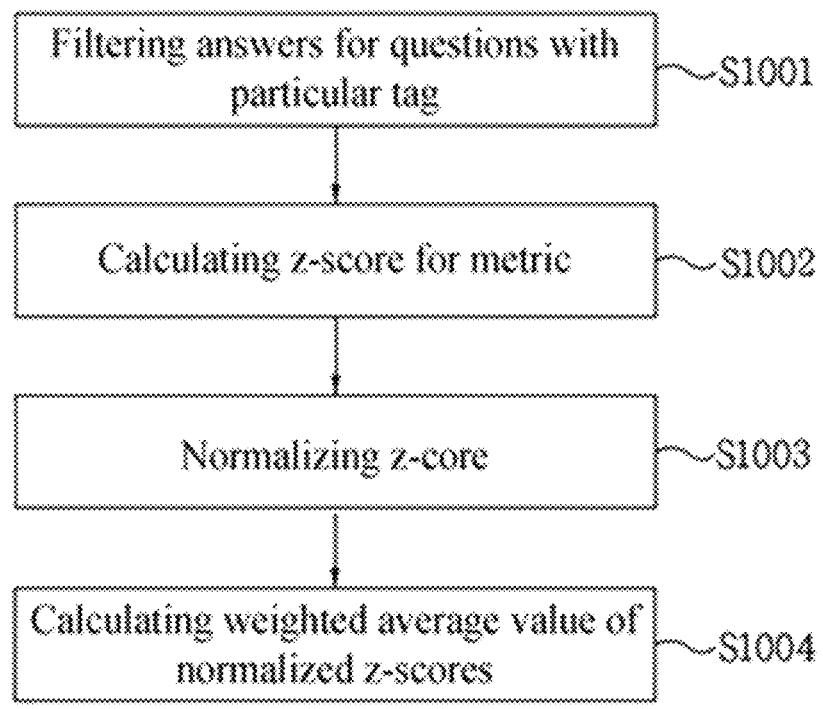
FIG. 11 is a flow chart of a calculation method for cognitive and behavioral diagnosis according to another example of the present invention.
Figure 12:
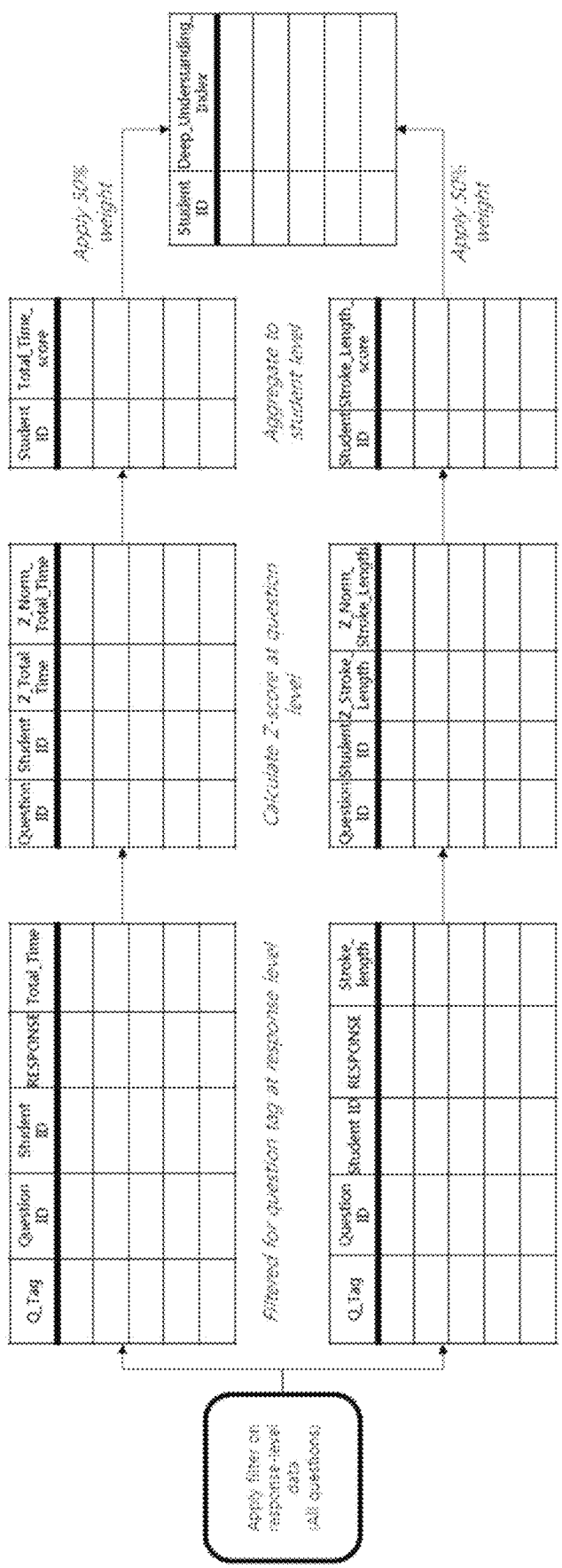
FIG. 12 shows an exemplary cognitive component calculation for cognitive and behavioral diagnosis according to another example of the present invention.

As an example performing the steps illustrated in FIG. 11, FIG. 12 shows a calculation flow to induce "deep understanding" among the cognitive and behavioral factors of Table 1. Table 1 includes metadata and behavioral metrics for a question as parameters to induce deep understanding. Specifically, concept_application_tag may be presented as the metadata and stroke length (stroke_length) and total time (total_time) may be considered as the behavioral metrics.

Referring to FIG. 12, first, a filter may be applied to response-level data for all questions to filter questions having a particular question tag (Q_tag) (e.g., concept_application_tag) at the response level. Next, z-score may be calculated for each behavioral metric at the question level, and the calculated z-score may be normalized to obtain a normalized z-score. The top of FIG. 12 shows Z_Total_Time as z-score for the total_time metric and Z_Norm_Total_Time as a normalized z-score. The bottom of FIG. 12 shows Z_Stroke_Length as z-score of the stroke length metric and Z_Norm_Stroke_Length as a normalized z-score. Next, the scores of the metrics may be aggregated at the student level and the metrics may be given a weighted average. For example, in FIG. 12, the total time metric may be given a 50% weight and the stroke length metric may be given a 50% weight to consequently calculate an index of "deep understanding" among the CBD factors.

Meanwhile, in regard to questions, a question that takes a long total time for an incorrect response and demands a long total input length for the correct response may be determined to be a question associated with grit. A question that takes a long total thinking time for the correct response and causes many long delays for the correct response may be determined to be a question demanding concentration. A question that generates a high number of strokes for the correct response and takes a long total time for the correct response may be determined to be a question demanding creativity. A question that takes a long initiation time for the correct response may be determined to be a question associated with speed of understanding. A question that demands a long total time and is associated with calculation may be determined to be a question associated with mental math speed. Additionally, a student's CBD factor may be evaluated at the test level, and the question's CBD factor may be evaluated at the question level. For example, it may be evaluated through a test whether the student has grit, and, when a thousand people solves various questions, it may be evaluated which questions demand grit.

Referring to FIG. 9 again, the diagnostic test apparatus may perform a step (S904) of providing a personalized study plan for the user based on a result of cognitive and behavioral analysis of the user.

For example, the personalized learning module (37) may provide a personalized study plan for the user by using analysis results of the cognitive and behavioral diagnostic module (36). The personalized learning module (37) may identify a particular set of questions that improves shortcomings of the user through practice and provide the identified particular set of questions to the user. Through the algorithm, the personalized learning module (37) may continuously learn the user's cognitive and behavioral analysis to make adjustments to improve quality of recommended practice questions over time.

Additionally, the personalized learning module (37) may perform repeated diagnosis and analysis of the user through machine learning using artificial intelligence and, accordingly, provide a personalized study plan to the user. Thus, it can be said that it is an optimized personalized learning module.

Specifically, the personalized learning module (37) may have an object of connecting cognitive and behavioral weaknesses identified by the cognitive and behavioral diagnostic module (36). Since the personalized learning module (37) may output a study plan at the user's level by using a method such as a multi-layer collaborative filtering recommendation engine that uses CBD indices, it can accurately derive practice questions that improve the user's cognitive weakness areas. Here, the CBD indices may be values for the above-mentioned CBD factors.

The personalized learning module (37) may obtain, as inputs, CBD indices analyzed by the cognitive and behavioral diagnostic module (36). For example, for each user (student), values of different CBD indices for each student and each question answered by the student may be provided as inputs. For example, values of CBD indices may be provided as in the matrix format shown below.

|         | Question |     |     |     |     |     |     |     |     |
| ------- | -------- | --- | --- | --- | --- | --- | --- | --- | --- |
| Student | Q1       | Q2  | Q3  | Q4  | Q5  | Q6  | Q7  | Q8  | Q9  |
| A       | 4.4      | 4.4 | 5.8 | 6.5 | 10  | 4.1 | 4.1 | 1.2 | 3.1 |
| B       | 3.5      | 7.7 | 7.1 | 1.4 | 5.8 | 6.8 | 3.0 | 4.7 | 1.8 |
| C       | 4.9      | 1.8 | 9.3 | 2.6 | 7.3 | 6.7 | 6.6 | 5.5 | 4.7 |
| D       | 7.9      | 6.8 | 7.5 | 2.5 | 3.9 | 9.5 | 9.7 | 7.4 | 7.0 |

Such a matrix may be constructed for each CBD index. Accordingly, for the eight CBD factors including confidence, grit, reasoning, concept memory, deep understanding, calculation ability, ability to understand question, and test-taking strategy derived from the cognitive and behavioral diagnostic module (36), a total of eight matrices may be provided.

Next, in order to determine i) similarity between questions and ii) similarity between students, the personalized learning module (37) may apply a similarity function, e.g., cosine similarity, to these matrices. Accordingly, the following two matrices may be created.

|   | A | B | C | D |
| - | - | - | - | - |
| A |   |   |   |   |
| B |   |   |   |   |
| C |   |   |   |   |
| D |   |   |   |   |

|    | Q1 | Q2 | Q3 | Q4 |
| -- | -- | -- | -- | -- |
| Q1 |    |    |    |    |
| Q2 |    |    |    |    |
| Q3 |    |    |    |    |
| Q4 |    |    |    |    |

The similarity values may be calculated by the following expression:

$$\text{similarity}(A, B) = \cos(\vec{A}, \vec{B}) = \frac{\vec{A} \cdot \vec{B}}{\|\vec{A}\|_2 * \|\vec{B}\|_2}$$

For example, as a calculated cosine similarity value gets closer to 1, the similarity between the two vectors gets higher. After calculating i) similarity between questions and ii) similarity between students, the personalized learning module (37) may calculate a cognitive gap metric for a specific question for a specific student by the following formula:

$$\text{Cognitive Gap} = \frac{\sum_v (CBD\ Index_{v,i} \cdot similarity_{u,v})}{\sum_v similarity_{u,v}}$$

wherein i may be called a question identifier and v may be called a student identifier.

The cognitive gap metric may be calculated for all of the above-mentioned eight CBD indices, and an aggregate of each question-student combination may be calculated. These are arranged by size such that questions having the highest aggregate cognitive gap metric for respective students may be most recommended for the students to improve their weaknesses.

As an another example, the cognitive gap metric may be calculated for all of the above-mentioned eight CBD indices, and the metrics may be arranged by size for each question-student combination such that questions having the highest cognitive gap metric for respective students may be most recommended for the students to improve their weaknesses. For example, when a similarity between questions and similarity between student have been calculated, the portion with the least similarity, i.e., the portion where the CBD factors show the greatest difference, may be considered first to recommend questions. That is, a question associated with grit (at the question level) may be recommended to a student considered to lack in grit (at the student level), and a question that other students lacking in grit had trouble with may be recommended to the student.

Additionally, by using such a similarity function, a question that students with similar behavioral characteristics usually presented an incorrect answer to and a question that students with a similar performance (score) presented an incorrect answer to may be recommended.

By using results of analysis of the test diagnostic module (35) and the cognitive and behavioral diagnostic module (36), which are preceding modules, the personalized learning module (37) may perform machine learning through repeated analysis and judgment on the user and accordingly provide a user-customized study plan by recommending the most appropriate questions for the user. For example, through machine learning, the personalized learning module (37) may identify users lacking in concept memory and/or questions demanding concept memory and also identify users lacking in deep understanding and/or question demanding deep understanding. The personalized learning module (37) may provide a user-customized study plan by, for example, providing a set of questions identified to be the ones demanding concept memory to the user lacking in concept memory, or a set of questions identified to be the ones demanding deep understanding to the user lacking in deep understanding. In addition, the personalized learning module (37) may be continuously learn analysis results from the cognitive and behavioral diagnostic module (36) so as to be adjusted to improve quality of recommended practice questions over time.

The descriptions of the methods and the process flow charts stated above are provided as illustrative examples only and are not intended to demand or imply that steps of various embodiments should be performed in the order in which they are set forth. As a skilled person in the art acknowledges, the steps of the above-mentioned embodiments may be performed in any order. Expressions such as "accordingly" and "next" are not intended to limit the order of the steps and are used to guide the reader through the descriptions of the methods.

Various exemplary logic blocks, modules, circuits, and algorithmic steps described in relation to the embodiments disclosed herein may be implemented by electronic hardware, computer software, and a combination thereof. For the purpose of clear illustration of the interchangeability between the hardware and software, various exemplary components, blocks, modules, circuits, and steps are described above generally in terms of their functionality.

Hardware used to implement various exemplary logics, logic blocks, modules, and circuits described in relation to the aspects disclosed herein may be implemented or performed by a general purpose processor, a digital signal processor (DSP), an application specific integrated circuit (ASIC), a field programmable gate array (FPGA) or another programmable logic device, discrete gate or transistor logic, discrete hardware components, or any combination thereof designed to perform the functions described herein. In addition, in one or more exemplary aspects, the described functions may be implemented by hardware, software, firmware, or a combination thereof. In case of implementation by software, the functions may be stored in a computer-readable medium as on one or more instructions or codes or transmitted via a computer-readable medium, and may be executed by a hardware-based processing unit. Computer-readable media may include computer-readable storage media corresponding to the type of media such as data storage media. In a non-limiting example, such computer-readable storage media may include RAMs, ROMs, EEPROMs, CD-ROMs or other optical disk storages, magnetic disk storages, or other magnetic storage devices, flash memories, or any other media that may be used to store a desired program code in a form of instructions or data structure or may be accessed by a computer.

The above-mentioned descriptions of the disclosed embodiments are provided for any skilled person in the art to carry out and use the present invention. Various modifications to these embodiments will be obvious to those skilled in the art, and the generic principles defined herein may be applied to other embodiments without departing from the spirit or scope of the invention. Accordingly, the present invention is not intended to be limited to the embodiments shown herein but is to be accorded the widest scope consistent with the following claims, and the principles and novel features disclosed herein.

The invention claimed is:

1. A diagnostic test method performed by a diagnostic test apparatus, the method comprising:
   obtaining input data from a smart pen based on information inputted by a user for at least one question with smart pen;
   creating first test behavior data on the user from the obtained input data, wherein the input data comprises coordinate values of points forming a plurality of strokes and information indicative of a time when the points were inputted, and wherein the created first test behavior data comprises a plurality of behavioral metrics; and
   determining at least one cognitive and behavioral diagnostic (CBD) factor of a plurality of first CBD factors of the user based on at least one of metadata on the at least one question and the created first test behavior data, wherein the determining comprises:
      obtaining second test behavior data for the at least one question from each of a plurality of users including the user;
      identifying at least one behavioral metric associated with the at least one CBD factor;
      calculating a score of the at least one behavioral metric, the score based on (i) a difference value between a value (X) of the at least one behavioral metric of the user based on the first test behavior data and a mean value ($\mu$) of the at least one behavioral metric of the plurality of users based on the second test behavior data, divided by (ii) a standard deviation value ($\sigma$) of the at least one behavioral metric of the plurality of users based on the second test behavior data;
      normalizing the score of the least one behavioral metric to a predetermined scale;
      calculating a weighted average of the normalized score based on a predetermined weight for the at least one behavioral metric;
      determining the at least one CBD factor of the user from the calculated weighted average;
   providing another question to the user based on the at least one CBD factor; and
   providing a personalized study plan to the user through machine learning based on at least one of the metadata on the at least one question or the created first test behavior data.

2. The method according to claim 1,
wherein the providing the personalized study plan to the user comprises:
   determining a plurality of second CBD factors for the at least one question for the plurality of users including the user;
   calculating, for each CBD factor of the plurality of second CBD factors, a similarity using at least two CBD factors associated with (i) at least two questions comprising the at least one question and (ii) two different users;
   calculating, for each CBD factor of the plurality of second CBD factors, a cognitive gap metric using the calculated similarity; and
   recommending the other question to the user based on the calculated cognitive gap metric.

3. The method according to claim 2,
wherein the recommending the other question to the user comprises:
   producing the calculated cognitive gap metric for each of combinations of the user and the at least one question;
   identifying the other question having the highest cognitive gap metric based on the calculated cognitive gap metric; and
   recommending the identified question to the user.

4. The method according to claim 1,
wherein the at least one CBD factor is selected from at least one of confidence, grit, reasoning, concept memory, deep understanding, calculation ability, ability to understand question, and test-taking strategy; and
each of the CBD factors is expressed with a function based on at least one of at least one different behavioral metric and metadata on the question.

5. The method according to claim 1,
wherein the at least one CBD factor is selected from at least one of confidence, grit, reasoning, concept memory, deep understanding, calculation ability, ability to understand question, and test-taking strategy; and
each of the CBD factors is expressed with a function based on at least one of at least one different behavioral metric and metadata on the question.

6. A non-transitory computer-readable medium storing software comprising instructions executable by one or more computers which, upon such execution, cause the one or more computers to perform operations comprising:
   obtaining input data from a smart pen based on information inputted by a user for at least one question with smart pen;
   creating first test behavior data on the user from the obtained input data, wherein the input data comprises coordinate values of points forming a plurality of strokes and information indicative of a time when the points were inputted, and wherein the created first test behavior data comprises a plurality of behavioral metrics; and determining at least one cognitive and behavioral diagnostic (CBD) factor of a plurality of first CBD factors of the user based on at least one of metadata on the at least one question and the created first test behavior data, wherein the determining comprises:

obtaining second test behavior data for the at least one question from each of a plurality of users including the user;

identifying at least one behavioral metric associated with the at least one CBD factor;

calculating a score of the at least one behavioral metric, the score based on (i) a difference value between a value (X) of the at least one behavioral metric of the user based on the first test behavior data and a mean value ($\mu$) of the at least one behavioral metric associated with the plurality of users based on the second test behavior data, divided by (ii) a standard deviation value ($\sigma$) of the at least one behavioral metric associated with the plurality of users based on the second test behavior data;

normalizing the score of the least one behavioral metric to a predetermined scale;

calculating a weighted average of the normalized score based on a predetermined weight for the at least one behavioral metric;

determining the at least one CBD factor of the user from the calculated weighted average;

providing another question to the user based on the at least one CBD factor; and providing a personalized study plan to the user through machine learning based on at least one of the metadata on the at least one question or the created first test behavior data.

7. The non-transitory computer readable medium according to claim 6, further comprising:

wherein the providing the personalized study plan to the user comprises:

determining a plurality of second CBD factors for the at least one question for the plurality of users including the user;

calculating, for each CBD factor of the plurality of second CBD factors, a similarity using at least two CBD factors associated with (i) at least two questions comprising the at least one question and (ii) two different users;

calculating, for each CBD factor of the plurality of second CBD factors, a cognitive gap metric using the calculated similarity; and recommending another question to the user based on the calculated cognitive gap metric.

8. The non-transitory computer readable medium according to claim 7, wherein the recommending the other question to the user comprises:

producing the calculated cognitive gap metric for each of combinations of the user and the at least one question;

identifying the other question having the highest cognitive gap metric based on the calculated cognitive gap metric; and recommending the identified question to the user.

9. The non-transitory computer readable medium according to claim 6, wherein the at least one CBD factor is selected from at least one of confidence, grit, reasoning, concept memory, deep understanding, calculation ability, ability to understand question, and test-taking strategy; and each of the CBD factors is expressed with a function based on at least one of at least one different behavioral metric and metadata on the question.

10. A system comprising:

one or more computers and one or more storage devices storing instructions that are operable, when executed by the one or more computers, to cause the one or more computers to perform operations comprising:

obtaining input data from a smart pen based on information inputted by a user for at least one question with smart pen;

creating first test behavior data on the user from the obtained input data, wherein the input data comprises coordinate values of points forming a plurality of strokes and information indicative of a time when the points were inputted, and wherein the created first test behavior data comprises a plurality of behavioral metrics; and determining at least one cognitive and behavioral diagnostic (CBD) factor of a plurality of first CBD factors of the user based on at least one of metadata on the at least one question and the created first test behavior data, wherein the determining comprises:

obtaining second test behavior data for the at least one question from each of a plurality of users including the user;

identifying at least one behavioral metric associated with the at least one CBD factor;

calculating a score of the at least one behavioral metric, the score based on (i) a difference value between a value (X) of the at least one behavioral metric of the user based on the first test behavior data and a mean value ($\mu$) of the at least one behavioral metric associated with the plurality of users based on the second test behavior data, divided by (ii) a standard deviation value ($\sigma$) of the at least one behavioral metric associated with the plurality of users based on the second test behavior data;

normalizing the score of the least one behavioral metric to a predetermined scale;

calculating a weighted average of the normalized score based on a predetermined weight for the at least one behavioral metric;

determining the at least one CBD factor of the user from the calculated weighted average;

providing another question to the user based on the at least one CBD factor; and providing a personalized study plan to the user through machine learning based on at least one of the metadata on the at least one question or the created first test behavior data.

11. The system according to claim 10, further comprising:

wherein the providing the personalized study plan to the user comprises:

determining a plurality of second CBD factors for the at least one question for the plurality of users including the user;

calculating, for each CBD factor of the plurality of second CBD factors, a similarity using at least two CBD factors associated with (i) at least two questions comprising the at least one question and (ii) two different users;
calculating, for each CBD factor of the plurality of second CBD factors, a cognitive gap metric using the calculated similarity; and
recommending another question to the user based on the calculated cognitive gap metric.

12. The system according to claim 11,
wherein the recommending the other question to the user comprises:
producing the calculated cognitive gap metric for each of combinations of the user and the at least one question;
identifying the other question having the highest cognitive gap metric based on the calculated cognitive gap metric; and
recommending the identified question to the user.

13. The system according to claim 10,
wherein the at least one CBD factor is selected from at least one of confidence, grit, reasoning, concept memory, deep understanding, calculation ability, ability to understand question, and test-taking strategy; and
each of the CBD factors is expressed with a function based on at least one of at least one different behavioral metric and metadata on the question.

\* \* \* \* \*